United States Patent
Sohn et al.

(10) Patent No.: US 7,037,502 B2
(45) Date of Patent: May 2, 2006

(54) PEPTIDE WITH THE AMINO ACID SEQUENCE OF KVLDGQDP HAVING ANTI-INFLAMMATORY PROPERTIES

(76) Inventors: Joon-Hong Sohn, c/o Dept. Ophthalmology, Asan Medical Center 388-1, Poongnap-dong, Songpa-gu, Seoul (KR) 138-040; Soo-Youl Kim, 182-7, Donggyo-dong, Mapo-gu, Seoul (KR) 121-818

( * ) Notice: Subject to any disclaimer, the term of this patent is extended or adjusted under 35 U.S.C. 154(b) by 545 days.

(21) Appl. No.: 10/115,704

(22) Filed: Apr. 4, 2002

(65) Prior Publication Data

US 2002/0192780 A1    Dec. 19, 2002

(30) Foreign Application Priority Data

Apr. 21, 2001    (KR)    .............................. 2001-21598

(51) Int. Cl.
*A61K 39/00*    (2006.01)
*C07K 1/00*    (2006.01)

(52) U.S. Cl. .................................... 424/185.1; 530/350
(58) Field of Classification Search ................ 530/350; 424/185.1
See application file for complete search history.

(56) References Cited

OTHER PUBLICATIONS

Mikayama et al. PNAS, 1993. 90: 10056-10060.*
Burgess et al J Cell Biol. 111:2129-2138, 1990.*
Lazar et al. Mol Cell Biol. 8:1247-1252, 1988.*
Whisstock et al Quarterly Review of Biophysics, 2003, 36, pp307-340.*

* cited by examiner

*Primary Examiner*—Christina Chan
*Assistant Examiner*—Michail A. Belyavskyi
(74) *Attorney, Agent, or Firm*—Barlow, Josephs & Holmes, Ltd.

(57) ABSTRACT

The present invention provides novel anti-inflammatory peptides having the amino acid of the SEQ ID NO:1 (KVLDPVKG); SEQ ID NO:2(KVLDGQDP) or SEQ ID No:3(DPVKG) containing inhibitory effects of transglutaminase and phospholipase $A_2$, their derivatives, pharmaceutical compositions containing the aforesaid peptides, and methods for preventing inflammation by using the same. The peptides, derivatives thereof, analogs thereof and the pharmaceutical compositions containing the same of the present invention show the higher anti-inflammatory activities than the existing known peptides or steroidal anti-inflammatory drugs, such as dexamethasone.

2 Claims, 5 Drawing Sheets

H&E staining of conjunctiva; normal control (A), inflamed conjunctiva by pollen with no treatment (B), with R2 (C), with E2 (D), with dexamethasone eye drops (E), and with Livostine (F)

(A)

(B)

(C)

(D)

(E)

(F)

PEPTIDE WITH THE AMINO ACID SEQUENCE OF KVLDGQDP HAVING ANTI-INFLAMMATORY PROPERTIES

TECHNICAL FIELD

The present invention provides novel anti-inflammatory peptides containing inhibitory effects of transglutaminase and phospholipase $A_2$, their derivatives, pharmaceutical compositions containing the aforesaid peptides, and methods for preventing inflammation by using the same.

BACKGROUND OF THE INVENTION

An inflammatory reaction is a complex biochemical and cytological phenomena that are manifested physiologically in tissue by edema, pain and leukocyte infiltration. The most effective drugs for the inflammation are glucocorticoids. Glucocorticoids, conventional anti-inflammatory steroidal drugs, have been proved to exhibit an excellent activity against rheumatoid arthritis and others by inhibiting or preventing various inflammatory reactions which is caused by radioactive, mechanical, chemical, infectious and immunological stimulation.

However, as the steroidal anti-inflammatory drugs are used widely, recently various harmful side effects caused by their abuse have resulted in serious problems. The steroidal anti-inflammatory drugs clinically causes two categories of side effects: the symptoms caused by a sudden break after a long-term administration and those others caused by too much use for a long time. After long-term administration of adrenocortical hormones, abruptly stopping it causes symptoms such as general prostration, fever, myalgia, arthralgia, and decrease of appetite, etc. as an outcome of the renal paresis. It also causes the increased opportunity for bacterial and viral infections, body weight increase, body form change and insomnia. So, there have been several problems for their applications, and thus it is desirable to develop a new anti-inflammatory drug without causing any side effects. To avoid these side effects, we need to develop specific inhibitors at certain inflammatory pathway. $PLA_2$ is the initial step enzyme to generate arachidonic acid from phospholipids that causes that inflammation at several steps later as prostaglandins and leukotrienes. Therefore, blocking of $PLA_2$ activation may be the best way to prevent inflammation. Indeed steroid is a powerful therapeutic approach although precise mechanism is not yet clear. One of the key mechanisms of steroid has been proposed that anti-inflammatory effect is mediated by induction of anti-inflammatory proteins. Glucocorticoid induces many proteins such as lipocortins, inhibitory proteins of phospholipase $A_2$ ($PLA_2$) (Flower, R. J. et al., *Nature* 278, 456–459, 1979). Numerous studies have revealed that their anti-inflammatory effects are mediated by the induction of lipocortins (Flower, R. J., et al., *Adv. Inflamm. Res.* 7, 61–69, 1984) and uteroglobins (Miele et al., *Endocr. Rev.* 8, 474–490, 1987). Lipocortins (annexins) are a class of proteins that share structural and functional features. In the functional feature, Miele et al. identified a region of sequence similarity between uteroglobin and lipocortin-1. Further they designed several synthetic peptides corresponding to the region of highest similarity between uteroglobin and lipocortin-1: nonapeptides, so called antiflammins (AFs), corresponding to uteroglobin residues 39–47 and lipocortin-1 residues 246–254. Both peptides were shown to be phospholipase $A_2$ ($PLA_2$) inhibitors in vitro and were effective in a classic model of acute inflammation in carrageenan-induced rat footpad edema (Miele et al., *Nature* 335, 726–730, 1988). However, it is controversial whether or not AFs have any inhibitory effect on $PLA_2$ as well as anti-inflammatory activity in vivo (Hope, W. C., et al. *Agents Actions* 34, 77–80, 1991; Marki, F., et al. *FEBS Lett.* 264, 171–175, 1990; Van Binsbergen, J., et al *FEBS Lett.* 247, 293–297, 1989). The existing antiflammin or $PLA_2$ inhibitor alone was not able to show potent anti-inflammatory effects like dexamethasone.

In the structural feature of lipocortins, most of them behave as extrinsic membrane proteins, which bind reversibly to phopholipid membranes in a manner that depends on calcium ions. Also during the epithelial cell differentiation, lipocortin-1 (annexin-1) becomes incorporated into the cornified cell envelope via cross-linking by transglutaminase (TGase) and cannot be extracted by SDS (Moore, K. G., et al *Exp. Cell Res.* 200, 186–195, 1992; Lee, C. H., et al., *FEBS Lett.* 477, 268–272, 2000). In the oral epithelium, it was found by sequencing proteins that lipocortin-1 constitutes about 10% of all the barrier envelope proteins. Thus lipocortin-1 itself possibly involves in the barrier formation as a major component containing anti-inflammatory function.

Another way of blocking $PLA_2$ can be inhibition of $PLA_2$ stimulation. Interestingly there is a report that $PLA_2$ was stimulated by TGase (Cordella-Miele, E, Miele, L, & Mukherjee, A. B. *J. Biol. Chem.* 265, 17180–17188, 1990). The increase of catalytic activity of $PLA_2$ was due to conformational change with intra molecular cross-linking by TGase. We have discovered that the inflammatory cytokines such as IFN- or TNF- could increase the expression of TGase (Kim, S.-Y, Jeong, E.-J., & Steinert, P. M. *J. Interferon and Cytokine Res. in press,* 2002). Consequently increase of TGase may cause increase of $PLA_2$ activity. Therefore, TGase inhibitors could inhibit inflammation through inhibition of $PLA_2$ stimulation.

As a result of the careful researches by the present inventors, sequence similarity between AFs and TGase substrate domain of elafin, which represents a core tetra peptide KVLD in AFs and DPVK in elafin. Elafin, also known as SKALP (skin-derived antileukoproteinase), is 6 kDa preform that can be activated to 3 kDa active form by proteolysis, which is specific and potent inhibitor of polymorphonuclear (PMN) cell-derived serine proteinases such as elastase and proteinase-3 (Molhuizen, H. O. F. et al., *J. Biol. Chem.* 268, 12028–32, 1993). Although KVLD is inactive as a $PLA_2$ inhibitor (Miele et al., *Nature* 335, 726–730, 1988), which could be active for the TGase inhibitor. The present inventors have also discovered that when an antiflammin contains lysine residues as an acyl acceptor, it competes with TGase substrate, and succeeded in synthesizing novel peptides from antiflammin based on this finding.

SUMMARY OF THE INVENTION

The objective of the present invention is to provide novel peptides having an excellent anti-inflammatory activity in comparison with the existing antiflammin, and without causing any of the side effects inherent in the steroidal anti-inflammatory drugs and also their medical use. In other words, the present invention provides synthetic peptides having amino acid sequence, SEQ ID NO: 1, 2 or 3 of the sequence listing.

DETAILED DESCRIPTION OF THE PREFERRED EMBODIMENTS

Figure 1:
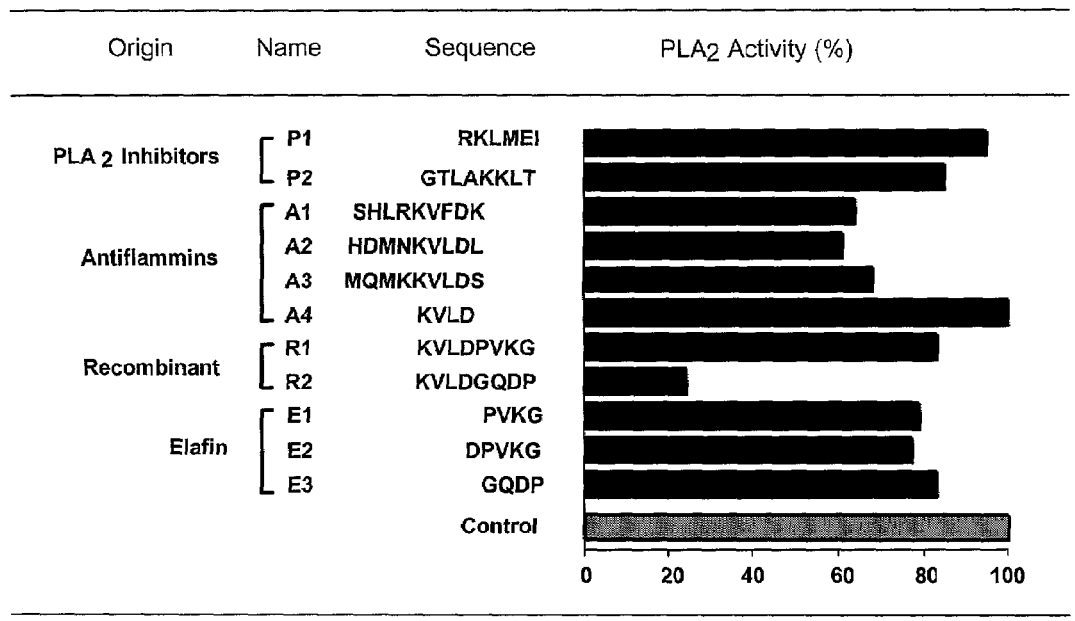
FIG. 1 is a graph showing the effects of the peptides of the present invention inhibiting the activity of $PLA_2$ in vitro.

The present invention provides peptides and peptide derivatives having the amino acid sequence of the SEQ ID NO:1 (KVLDPVKG); SEQ ID NO:2 (KVLDGQDP) or SEQ ID No:3 (DPVKG) of the sequence listing, and analogous peptides, which exhibit anti-inflammatory activity and inhibitory effects of transglutaminase and phospholipase $A_2$.

The present invention also provides pharmaceutical compositions comprising said peptides, peptides derivatives and peptides analog and a method for inhibiting inflammation utilizing the same.

The peptides of the present invention can vary within the range wherein their activity is maintained. At least one side chain amine group of the peptides for example, can be acylated or arylated, or at least one hydroxyl group of said peptides can be esterified to an alkyl group or an aryl group.

In one embodiments, the present invention provides for analog and/or derivatives of said peptides(SEQ ID NO: 1, 2 or 3) as anti-inflammatory agents, such as those in which the amino-terminal end of the peptide is modified by addition of an R—(C=O)— group in which R is selected from the group consisting of an alkyl, a cycloalkyl, an aryl and heteroaryl, wherein the aryl or heteroaryl is either unsubstituted or substituted with a halogen, methoxy, amino or alkyl functional group; or in which the carboxy-terminal end of the peptides can also be modified by addition of an R'-group in which R'-is selected from the group consisting of an amine, an amide, an alkyl ester, a cycloalkyl ester, an aryl ester, or a heteroaryl ester, wherein the aryl ester or heteroaryl ester can be either unsubstituted or substituted with a halogen, methoxy, amino, or alkyl functional group, or in which both ends of the peptide can be so modified, provided that said analogs and/or derivatives exhibit anti-inflammatory activity. It is well known to those who skilled in the art that these analogs or derivatives are also within the scope of the present invention. As used herein, the terms "aryl" and "aryl ester" are intended to encompass groups containing a 6- or 7-unit ring structure, and include, e.g., pyridinium, imidazolium and quinoxaline groups.

In other embodiments, the present invention provides for analogs of said peptides (SEQ ID NO:1, 2 or 3) as anti-inflammatory agents in which any one or more of the amino acid residues of said peptides(SEQ ID NO:1, 2 or 3) can be substituted by different amino acid analogs or mimic, e.g., to produce carbazates or tertiary centers, the incorporation of which serves to avoid or reduce proteolytic cleavage of the peptide, provided that said analogs exhibit anti-inflammatory activity.

The peptides of the present invention may be prepared by any method known in the art. For example, and not by way of limitation, the peptides may be synthesized: (i) by cleavage from a larger peptide; (ii) by recombinant DNA expression methods; and (iii) by chemical synthesis, including solid phase techniques as described by Barany and Merrifield(1980, in "*The Peptides*" Vol 2. Gross and Meienhofer. Eds., Academic Press, N.Y.), preferably by an automatic peptide synthesizer.

As to the recombinant DNA expression method, the conventional method comprising the steps of synthesizing the DNA corresponding to the amino acid sequence of the peptides of the present invention; attaching a linker having restriction enzyme cleavage site to the termini of said DNA; and then preparing a recombinant vector by ligating said DNA-linker molecule into a conventional vector having a regulatory promoter.

The peptides of the present invention can be produced, by transforming the resultant recombinant vector into a suitable host and then expressing the peptides within the transformed organism by a biotechnological process. The examples of the vectors include a conventional vectors such as made from plasmid, cosmid, YAC, virus etc. and the examples of the hosts include bacteria, yeast, fungi, animal cells, plant cells, and others. For the purposes of the separation and purification of the resultant peptides, signal sequences for extracellular destination can be ligated to the synthetic DNA, or the peptides can be produced in the form of fusion proteins by linking a portion of a gene or whole gene which is originated from the host to the aforementioned DNA. After separation and purification, the fused proteins can be cleaved and separated by chemical or enzymatical procedures.

The peptides of the present invention exhibit potent anti-inflammatory activity, and may also be administered into a subject together with biologically active agents, such as biologically active compounds or other peptides, or in parallel with other kinds of anti-inflammatory drugs.

Further, the present invention provides a pharmaceutical composition for anti-inflammation, comprising an effective amount of the peptide, peptide derivative or peptide analog of the aforementioned peptides and pharmaceutically acceptable carrier. The said pharmaceutical compositions of the present invention may contain one or more of the conventional pharmaceutically acceptable solvents, surfactants, oil or anti-oxidizers for their chemical stability. The said compositions contain the said synthetic peptides by 0.00001~50% in the basis of weight of the total composition, and preferably by 0.001~30%. If it is less than 0.00001 wt %, the desirable activity of the present invention is insignificantly low, if more than 50 wt %, the desirable activity of the present invention doesn't increase correspondingly to the increase of the amount.

The compositions of the present invention may be administered by any suitable and accepted route of drug administration, including intravenous, subcutaneous, intradermal, intranasal, inhalation (e.q., by lung aerosol or lavage), intramuscular, intraocular, intraperitoneal injection, peritoneal lavage, cardiac puncture, cardiac catheter injection, oral, intrathecal or intraventricular injection, spinal column or cranial cavity injection, vaginal or rectal(e.g., by suppository), dermal patch or topical ointment, and may be comprised in any suitable pharmaceutical carrier, including aqueous solution, microcapsules, liposomes, or via a sustained-released implant, including hydrophilic or hydrophobic carrier-based implants.

The administration dosage will differ depending on age, gender, body weight, symptoms, treatment effect, administration route, treatment time and substance administrated with. But it is desirable to administer in an effective amount to inhibit the inflammation, desirably 0.001 g~2 g/kg for each time for adults. It is well known to the art that the peptides may be modified by aforementioned method to prevent proteolysis during their delivery, depending on the administration route, for example oral administration.

Such a composition may also include adjuvants, such as preservatives, humectants, emulsifiers, dispersers and stabilizers (for example, arginine and aspartic acid).

The present invention also provides a method for inhibiting an inflammatory response that is associated or caused by inflammatory diseases, comprising the step of exposing humans or animals to an effective amount of the peptide, peptide derivative or peptide analog aforementioned.

The examples of the inflammatory response that is associated or caused by inflammatory diseases including autoimmune diseases such as ulcerative colitis, rheumatoid arthritis, scleroderma, inflammatory lung disease, celiac disease, systemic lupus, myasthenia gravis and diabetes; skin allergy, pimples or trauma. The method of the present invention may be also used in all of the diseases or symptoms in which the peptide of the present invention are effective, such as various degenerative diseases, painful diseases or nervous diseases.

The invention will now be explained in greater detail by way of the following examples, with understanding that the invention is in no way restricted by these examples.

EXAMPLES

Example 1

(1) Synthesis of the Peptides

According to the sequences described in Table 1, the peptides of the present invention were synthesized by an automatic peptide synthesizer, and the synthesized peptides were purified by using a C8 reverse phase high performance liquid chromatography. Further, by using abovementioned method, known peptides such as antiflammin were synthesized, and their sequences are as shown in Table 2.

TABLE 1

| Peptide | Amino acid sequence |
| --- | --- |
| SEQ ID NO:1 | KVLDPVKG |
| SEQ ID NO:2 | KVLDGQDP |
| SEQ ID NO:3 | DPVKG |

TABLE 2

| Peptide | Amino acid sequence |
| --- | --- |
| SEQ ID NO:4(PLA$_2$ inhibitor) | PKLMEI |
| SEQ ID NO:5(PLA$_2$ inhibitor) | GTLAKKLT |
| SEQ ID NO:6(antiflammin) | SHLRKVFDK |
| SEQ ID NO:7(antiflammin) | HDMNKVLDL |
| SEQ ID NO:8(antiflammin) | MQMKKVLDS |
| SEQ ID NO:9(antiflammin) | KVLD |
| SEQ ID NO:10(TGase inhibitor) | PVKG |
| SEQ ID NO:11(TGase inhibitor) | GQDP |

(2) Inhibitory Effect of Synthetic Peptides on PLA$_2$ and TGase Activities In Vitro Inhibitory Effect of Synthetic Peptides on PLA$_2$ It has been examined whether synthetic peptides contain inhibitory effect on PLA$_2$ activity. A established PLA$_2$ assay method was used to determine the enzymatic activity by measuring the release [$^{14}$C]-arachidonic acid from 1-acyl-2-[1-$^{14}$C]arachidonic acid-glycerophospho-ethanolamine (Biochem. Pharmacol. 54, 259–268, 1997). To determine the inhibitory activity, 0.18 Unit PLA$_2$ (Bovine pancreas, EC 3.1.1.4, Sigma; 1.0 unit will hydrolyze 1.0 mole of L-phosphatidylcholine to L-lysophosphatidylcholine and a fatty acid per min. at pH 8.0 at 37° C.) was preincubated for 15 minutes with the synthetic peptides ($1 \times 10^{-8}$ M) at 37° C. in 60 l before adding 1-acyl-2-[1-$^{14}$C]arachidonic acid-glycerophospho-ethanolamine. The control was also PLA$_2$ preincubated with buffer. After pre-incubation, PLA$_2$ activity was assayed using sonicated liposomes, prepared as established method (Biochem. Biophys. Acta. 1083, 80–88, 1991). 40 l of 1-acyl-2-[1-$^{14}$C]arachidonic acid-glycerophospho-ethanolamine (about $2 \times 10^5$ dpm) was added in pre-incubated mixture, and incubated for 1 hr at 37° C. The reaction was terminated by adding 0.75 ml of Dole's reagent (78% n-heptane, 20% propan-2-ol, and 2% 2M aqueous H$_2$SO$_4$), and the liberated [$^{14}$C]-arachidonic acid was extracted as follows. 0.25 ml of H$_2$O was added into the incubated mixture, vortexed, and centrifuged at 1,200×g for 5 min. Then upper phase was transferred to a new tube that contained 100 mg of silica gel (230–400 mesh, Sigma) and 0.75 ml of n-haptene. The sample was vortexed and centrifuged at 1,200×g for 5 min. The supernatant was collected for scintillation counting (Biochem. Pharmacol. 54, 259–268, 1997). Values are means for three determinations (SD<10%).

For inhibitory test of the peptides given, each value is the mean of data from three separate experiments (S.D.<10%). The value of PLA$_2$ activity incubated without peptides was determined as 100% PLA$_2$ activity that is 5.57 pmole arachidonyl/hr. % Inhibition was shown in FIG. 1.

Inhibitory Effect of Synthetic Peptides on TGase

It is needed to inhibit the activity of TGase in order to secure maximum anti-inflammatory activity since the TGase activates PLA$_2$. A established TGase assay method was used to determine the enzymatic activity by measuring the incorporation of [1,4]$^{14}$C-putrescine into succinylated casein (Folk J E., et al., *Transglutaminase. Methods in Enzymol* 1985; 113; 358–375).

Figure 2:
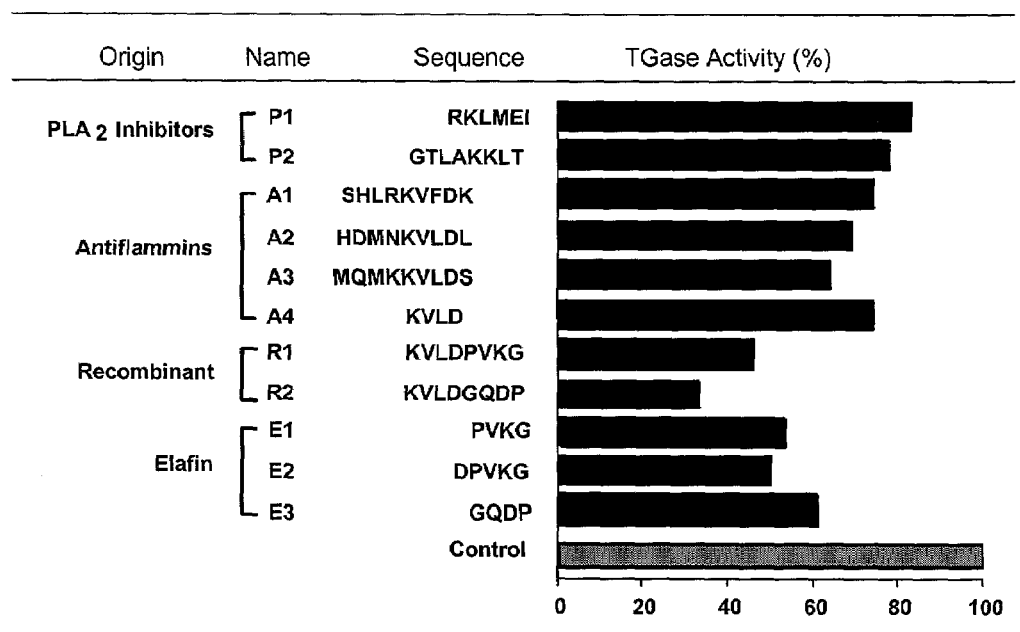
FIG. 2 is a graph showing the effects of the peptides of the present invention inhibiting the activity of TGase in vitro.

To determine the inhibitory activity, 0.001 U TGase (Guinea pig liver, EC 2.3.2.13, Sigma; 1.0 unit will catalyze the formation of 1.0 mole of hydroxamate per min. from N--CBZ-Gln-Gly and hydroxylamine at pH 6.0 at 37° C.) was preincubated for 15 minutes with the synthetic peptides in 0.1 ml ($1 \times 10^{-8}$ M) at 37° C. before adding the TGase/peptide mixture to the substrate solution (0.5 ml) containing 0.1 M Tris-acetate pH 7.5, 1% succinylated casein, 1 mM EDTA, 10 mM CaCl$_2$, 0.5% lubrol PX, 5 mM DTT, 0.15M NaCl and 0.5 mCi $^{14}$C-putrescine [Dupont-New England Nuclear, Wilmington, Germany (118 Ci/mole)]. Following incubation at 37° C. for one hour, the reaction was terminated by addition of 4.5 ml of cold (4° C.) 7.5% TCA. The TCA-insoluble precipitates were collected onto GF/A glass fiber filters, washed with cold 5% TCA, dried and counted. The resulting TGase inhibiting activity was as shown in FIG. 2. The control was also TGase preincubated with buffer. Values are means for three determinations.

For inhibitory test of the peptides given, each value is the mean of data from three separate experiments (S.D.<10%). The value of TGase activity incubated without peptides was determined as 100% TGase activity that is 4.89 pmole putrescine/hr. % Inhibition was shown in FIG. 2.

Inhibitory Effect of Synthetic Peptides on PLA$_2$ Activated by TGase

A series of synthetic peptides (1×10$^{-8}$ M) were pre-incubated with 0.001 Unit TGase (Guinea pig liver, Sigma) in 60 l of assay buffer (75 mM Tris-Cl, pH 9.0, 5 mM CaCl$_2$, 1 mg/ml fatty acid free bovine serum albumin) for 15 min at 37° C. We employed a negative control as assay buffer without TGase, and a positive control as TGase without peptides. After pre-incubation, 40 l of 1-acyl-2-[1-$^{14}$C] arachidonic acid-glycerophospho-ethanolamine (about 2×10$^5$ dpm) was added in pre-incubated mixture, and incubated for 1 hr at 37° C. The reaction was terminated by adding 0.75 ml of Dole's reagent, and followed the same procedure described as above.

PLA$_2$ activity was increased about 2-fold after TGase treatment, demonstrating that TGase activates the PLA$_2$ activity. For inhibitory test of the peptides given, each value is the mean of data from three separate experiments (S.D.<10%). The increased PLA$_2$ activity by TGase was determined as 100% that was 11.22 pmole arachidonyl/hr. % Inhibition was shown in FIG. 3.

Figure 3:
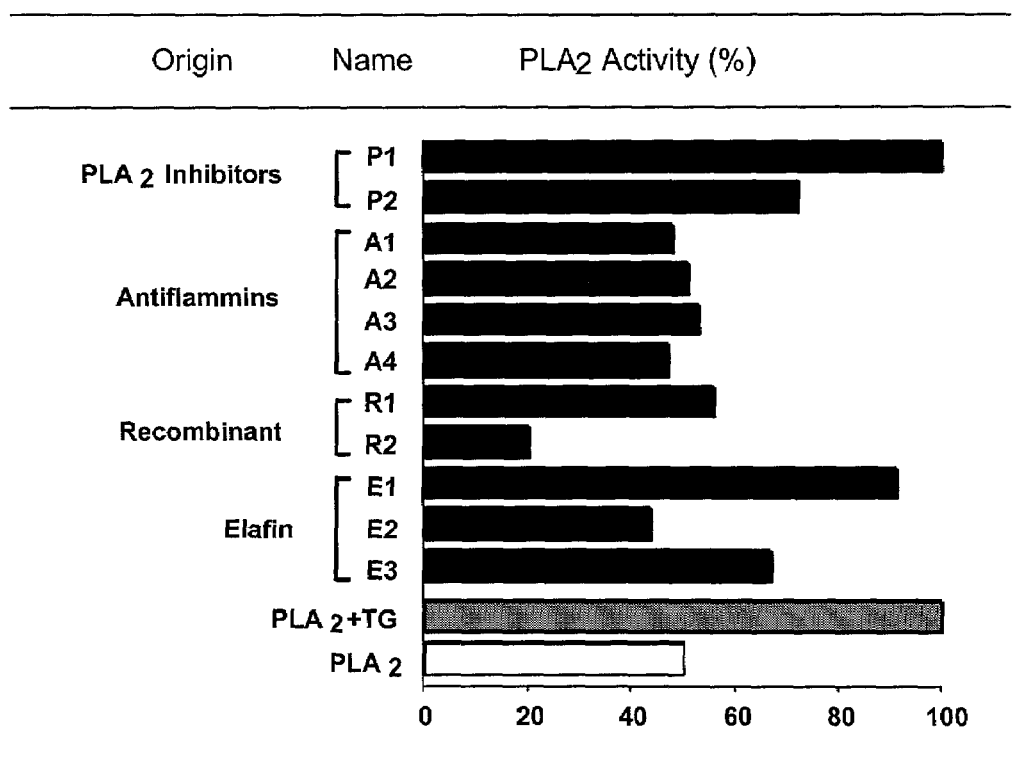
FIG. 3 is a graph showing the effects of the peptides of the present invention inhibiting the activity of $PLA_2$ activated by TGase in vitro.

As shown in FIGS. 1, 2 and 3, the R1 and R2 peptides of the present invention significantly reduced the PLA$_2$ and TGase activities in comparison with the peptides known in PLA$_2$ inhibitors.

Example 2

In Vivo Measurement of Anti-inflammatory Activity

The peptides of the present invention were analyzed in experimental model of allergic conjunctivitis to ragweed (giant ragweed; *Ambrosia trifida*) in guinea pig. Hartley strain of guinea pig was selected according to previous reports of conjunctival anaphylaxis (Calonge M., et al., *Acta Ophthalmol* 68; 470–476, 1990) and females were chosen based on the sex dimorphism of ocular mucosal immunity with the protective role of male hormones (Saruya S., et al., *Act Soc Ophthalmol Jap* 72; 833–845, 1968). The conjunctival redness and edema are main signs of seasonal allergic conjunctivitis and eosinophil infiltration is the hallmark of the conjunctival histology in patients with allergic conjunctivitis (Abelson M B., et al., *Arch Ophthalmol.* 101; 555–556, 1983; Butrus S I., et al., *Int. Ophthalmol. Clin.* 28; 324–328, 1988)

(1) Animals

86 Hartley female guinea pigs, 200–250 g were housed in the animal facilities of the Asan Institute for Life Sciences (Korea), given guinea pig chow and water ad libitum, and cared for in accordance with the Declaration of Helsinki and the National Institute of Health Guide to the Care and Use of the Laboratory Animals (Korea).

(2) Immunization and Challenge

Giant ragweed pollen, *Ambrosia trifida*, 1.0–1.5 mg (Sigma) was delivered into the nostrils and the inferior conjunctival fornices of the 84 animals on days 1 to 5 and 8 to 12, once a day with an Eppendorf micropipette calibrated to 10 μl. On day 15, immunized guinea pigs were divided 14 groups, 6 for each group. 11 anti-inflammatory peptides including new recombinants, dexamethasone eye drop (Maxidex, 0.1% dexamethasone, Alcon) and anti-histamine eye drop (Livostin, levocabastine, Janssen) were used for 13 groups, and no treatment for one group. Normal controls were employed as 6 non-immunized and non-treated guinea pigs. All immunized guinea pigs were challenged with 1.0–1.5 mg of ragweed pollen powder delivered to the inferior conjunctival fornice on day 15. All the procedures were followed experimental model of allergic conjunctivitis described by Merayo-Lloves et al (*Experimental model of allergic conjunctivitis to ragweed in guinea pig. Curr. Eye Res.* 14; 487–494, 1995).

(3) Treatment Using Peptides, Dexamethasone Eye Drop and Anti-Histamine Eye Drop Anti-inflammatory peptides were resolved in sterile saline (100 μmol/40 μl concentration). All peptides and dexamethasone eye solutions were challenged 3 hour prior to the last pollen application on day 15, 10 minutes after pollen application, and 4 times thereafter at the 3 hour interval.

(4) Clinical Evaluation

Conjunctival edema and redness were judged in room light and under an operating microscope (Zeiss, Germany). The evaluation was performed in a masked fashion at 20 min after allergen challenge and each clinical sign was scored on a scale 0–4+ (0 absent, 1+ minimal, 2+ mild, 3+ moderate, 4+ severe), adapted for guinea pig from previous report (Merayo-Lloves et al: *Experimental model of allergic conjunctivitis to ragweed in guinea pig. Curr. Eye Res.* 14; 487–494, 1995). Clinical scores of each group (12 eyes in each group) were analyzed.

(5) Histology

The orbits were excentrated after the animals were killed with CO$_2$ asphyxia, and specimens were prepared for light microscopic examination. Sectioned specimens were stained with hematoxylin-eosin.

Eosinophils in the standardized fields of conjunctival epithelium, the immediate subepithelial, and the stroma were counted in three non-consecutive fields (magnification ×400) for each treatment in each experiment (12 eyes in each group).

(6) Results

Clinical Signs

Figure 4:
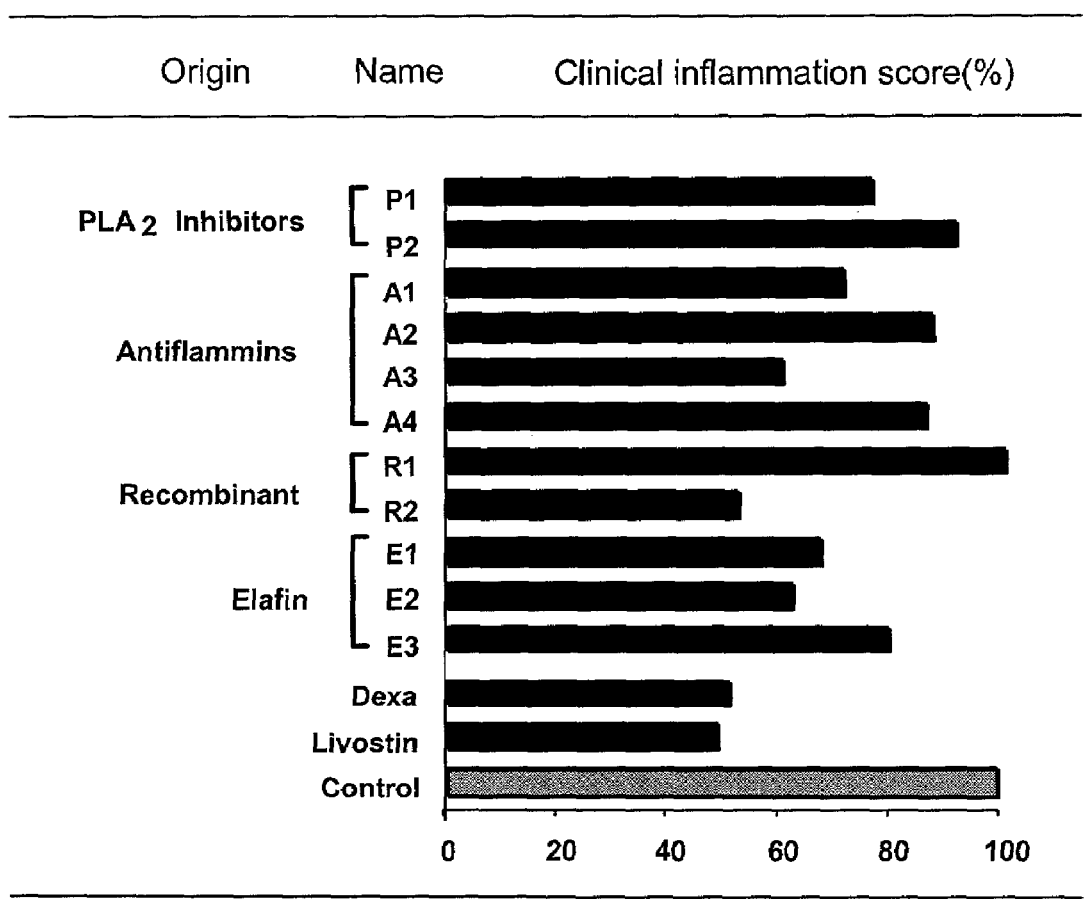
FIGS. 4 and 5 are graphs showing the results of the experiments with the peptides of the present invention for anti-inflammatory activity in the allergic conjunctivitis model using guinea pigs.

Conjunctival redness and edema scores are shown in FIG. 4 and Table 3.

Clinically, RKLMEI (SEQ ID NO:4), SHLRKVFDK (SEQ ID NO:6), MQMKKVLDS (SEQ ID NO:8), KVLDGQDP (SEQ ID NO:2), PVKG (SEQ ID NO:10), DPVKG (SEQ ID NO:3), and dexamethasone (a steroidal anti-inflammatory drug) showed statistically significant difference from other groups (n=12, P<0.01, SD<10%, Mann-Whitney test). Especially, the one of the peptide of the present invention (SEQ ID NO:2), dexamethasone and Livostin (an anti-histamine eye drop) were most effective.

TABLE 3

Statistical evaluation of clinical scores (Mann-Whitney test)

| | | Compared | | |
|---|---|---|---|---|
| Name | Sequence | to No treatment group | to Dexamethasone | to Livostine |
| P1 | RKLMEI | 0.009 | 0.001 | 0.003 |
| P2 | GTLAKKLT | 0.279 | 0.000 | 0.000 |
| A1 | SHLRKVFDK | 0.003 | 0.007 | 0.009 |
| A2 | HDMNKVLDL | 0.382 | 0.002 | 0.003 |
| A3 | MQMKKVLDS | 0.000 | 0.089 | 0.043 |
| A4 | KVLD | 0.082 | 0.000 | 0.000 |
| R1 | KVLDPVKG | 0.965 | 0.000 | 0.000 |
| R2 | KVLDGQDP | 0.000 | 0.796 | 0.515 |
| E1 | PVKG | 0.001 | 0.017 | 0.012 |

TABLE 3-continued

Statistical evaluation of clinical scores (Mann-Whitney test)

| Name | Sequence | Compared to No treatment group | to Dexamethasone | to Livostine |
|---|---|---|---|---|
| E2 | DPVKG | 0.000 | 0.050 | 0.039 |
| E3 | GQDP | 0.016 | 0.000 | 0.002 |
| Dexamethasone | | 0.000 | | |

Histological Signs

Figure 5:
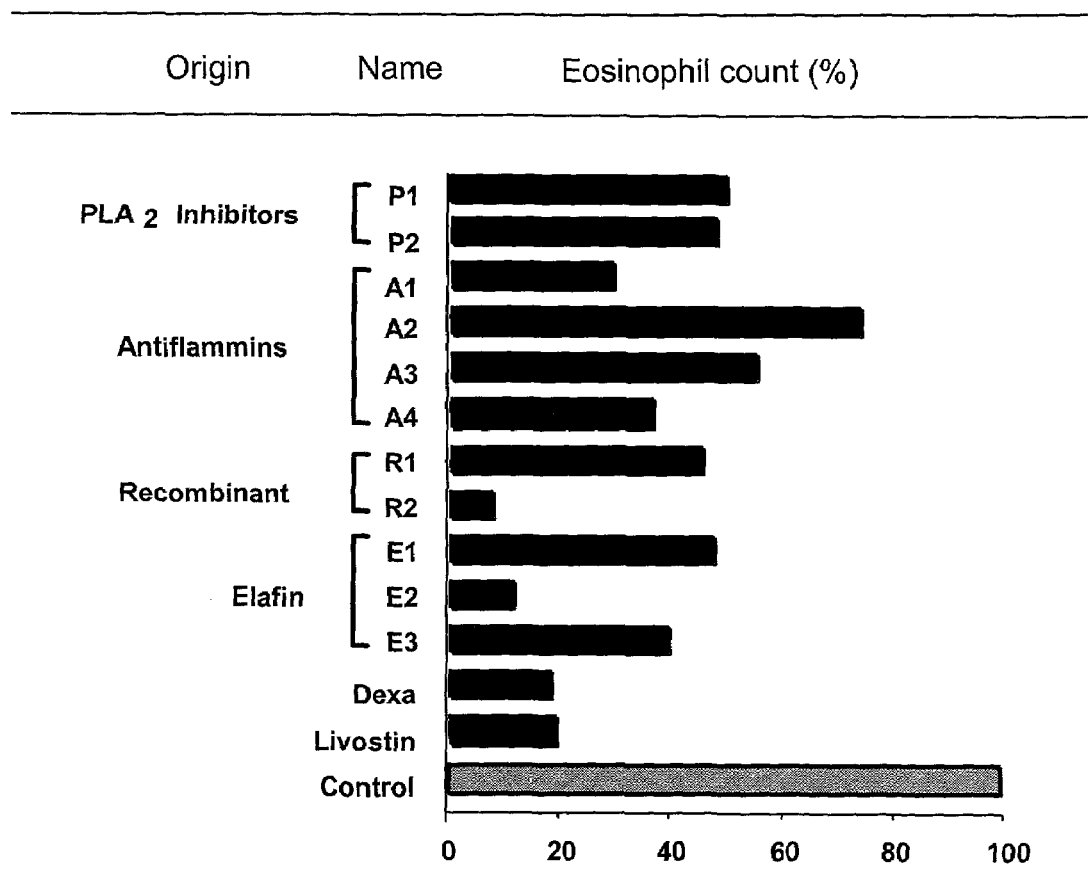
Figure 6:
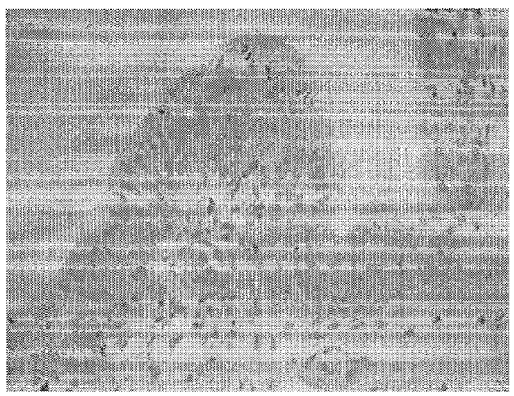
FIG. 6 is showing H & E staining of conjunctiva. Eosinophils in the standardized three fields of conjunctival epithelium and the stroma were counted (×400).
Figure 6:
Figure 6:
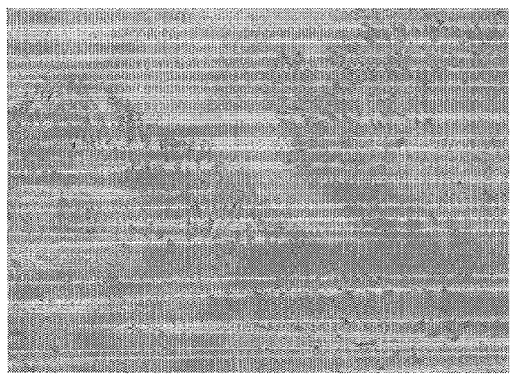
Figure 6:
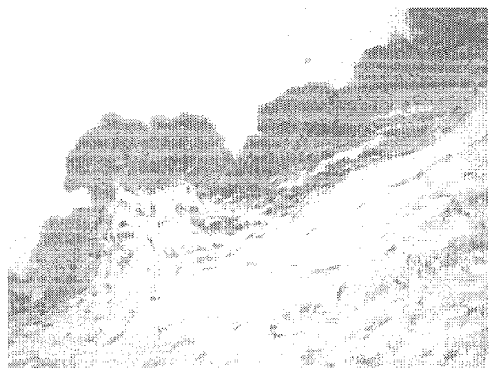
Figure 6:
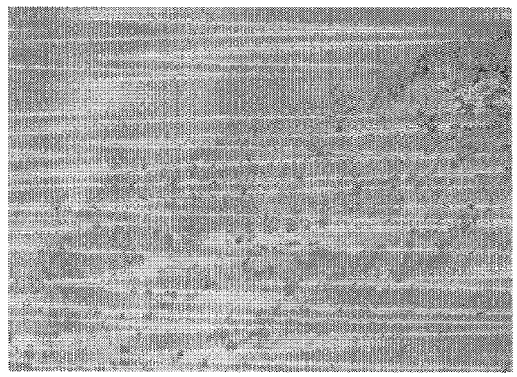
Figure 6:
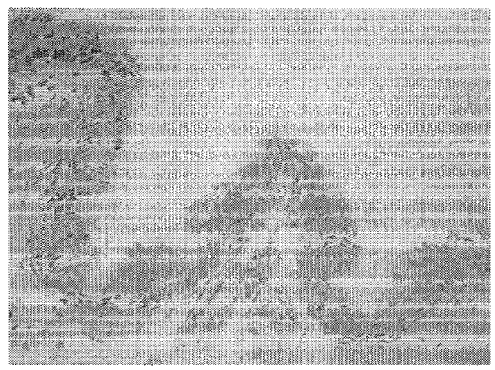

The histological results are also shown in FIG. 5, FIG. 6 and Table 4. Most anti-inflammatory peptides except HDM-NVLDL (SEQ ID NO:7) inhibited eosinophil infiltration (n=12, P<0.01, SD<10%, Mann-Whitney test). Especially, KVLDGQDP (SEQ ID NO:2) and DPVKG (SEQ ID NO:3) of the present invention, dexamethasone (a steroidal anti-inflammatory drug) and Livostin (an anti-histamine eye drop) showed statistically significant difference from other groups. Among those, KVLDGQDP (SEQ ID NO:2) of the present invention was the most effective.

TABLE 4

Statistical evaluation of eosinophil count (Mann-Whitney test)

| Name | Sequence | Compared to No treatment group | to Dexamethasone | to Livostine |
|---|---|---|---|---|
| P1 | RKLMEI | 0.002 | 0.000 | 0.000 |
| P2 | GTLAKKLT | 0.004 | 0.000 | 0.000 |
| A1 | SHLRKVFDK | 0.000 | 0.004 | 0.006 |
| A2 | HDMNKVLDL | 0.161 | 0.000 | 0.000 |

TABLE 4-continued

Statistical evaluation of eosinophil count (Mann-Whitney test)

| Name | Sequence | Compared to No treatment group | to Dexamethasone | to Livostine |
|---|---|---|---|---|
| A3 | MQMKKVLDS | 0.007 | 0.000 | 0.000 |
| A4 | KVLD | 0.001 | 0.028 | 0.045 |
| R1 | KVLDPVKG | 0.002 | 0.001 | 0.002 |
| R2 | KVLDGQDP | 0.000 | 0.001* | 0.002* |
| E1 | PVKG | 0.002 | 0.000 | 0.000 |
| E2 | DPVKG | 0.000 | 0.028 | 0.060 |
| E3 | GQDP | 0.001 | 0.007 | 0.000 |
| Dexamethasone | | 0.000 | | 0.932 |

*better than dexamethasone and Livostine

As shown herein, the peptides of the present invention (SEQ ID NO: 1, 2 or 3) have exhibited a excellent anti-inflammatory activity in comparison with other known peptide sequences. Especially, SEQ ID NO:2 and 3 of the present invention have exhibited much higher activity than the steroidal anti-inflammatory dexamethasone. Thus, the peptides of the present invention (SEQ ID NO:1, 2 or 3) show a excellent anti-inflammatory activity without showing any of the harmful side effects of the steroidal anti-inflammatory drugs, such as dexamethasone.

EFFECT OF THE INVENTION

The peptides of the present invention (SEQ ID NO:1, 2 and 3 of the sequence listing) are novel, show much higher anti-inflammatory activities than the conventional antiflammins and other anti-inflammatory drugs, thus are useful for pharmaceutical purposes.

What is claimed is:

1. An isolated and purified peptide consisting of the amino acid sequence of the SEQ ID NO:2 and having anti-inflammatory activity and inhibitory effects on transglutaminase and phospholipase $A_2$.

2. A pharmaceutical composition for anti-inflammation and inhibitory effects on trausgiutaminase and phospholipase $A_2$ comprising the peptide of claim 1 and a pharmaceutically acceptable carrier.

* * * * *

SEQUENCE LISTING

```
<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: SYNTHETIC

<400> SEQUENCE: 1

Lys Val Leu Asp Pro Val Lys Gly
1               5

<210> SEQ ID NO 2
<211> LENGTH: 8
<212> TYPE: PRT
<213> ORGANISM: Artificial Sequence
<220> FEATURE:
<223> OTHER INFORMATION: SYNTHETIC

<400> SEQUENCE: 2

Lys Val Leu Asp Gly Gln Asp Pro
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: SYNTHETIC

<400> SEQUENCE: 3

Asp Pro Val Lys Gly
1               5

<210> SEQ ID NO 4
<211> LENGTH: 6
<212> TYPE: PRT
<213> ORGANISM: Artificial Sequence
<220> FEATURE:
<223> OTHER INFORMATION: SYNTHETIC

<400> SEQUENCE: 4

Pro Lys Leu Met Glu Ile
1               5

<210> SEQ ID NO 5
<211> LENGTH: 8
<212> TYPE: PRT
<213> ORGANISM: Artificial Sequence
<220> FEATURE:
<223> OTHER INFORMATION: SYNTHETIC

<400> SEQUENCE: 5

Gly Thr Leu Ala Lys Lys Leu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: SYNTHETIC

<400> SEQUENCE: 6

Ser His Leu Arg Lys Val Phe Asp Lys
1               5

<210> SEQ ID NO 7
<211> LENGTH: 9
<212> TYPE: PRT
<213> ORGANISM: Artificial Sequence
<220> FEATURE:
<223> OTHER INFORMATION: SYNTHETIC

<400> SEQUENCE: 7

His Asp Met Asn Lys Val Leu Asp Leu
1               5

<210> SEQ ID NO 8
<211> LENGTH: 9
<212> TYPE: PRT
<213> ORGANISM: Artificial Sequence
<220> FEATURE:
<223> OTHER INFORMATION: SYNTHETIC

<400> SEQUENCE: 8

Met Gln Met Lys Lys Val Leu Asp Ser
1               5
```

-continued

```
<210> SEQ ID NO 9
<211> LENGTH: 4
<212> TYPE: PRT
<213> ORGANISM: Artificial Sequence
<220> FEATURE:
<223> OTHER INFORMATION: SYNTHETIC

<400> SEQUENCE: 9

Lys Val Leu Asp
1

<210> SEQ ID NO 10
<211> LENGTH: 4
<212> TYPE: PRT
<213> ORGANISM: Artificial Sequence
<220> FEATURE:
<223> OTHER INFORMATION: SYNTHETIC

<400> SEQUENCE: 10

Pro Val Lys Gly
  1

<210> SEQ ID NO 11
<211> LENGTH: 4
<212> TYPE: PRT
<213> ORGANISM: Artificial Sequence
<220> FEATURE:
<223> OTHER INFORMATION: SYNTHETIC

<400> SEQUENCE: 11

Gly Gln Asp Pro
  1
```